(12) United States Patent
Herron et al.

(10) Patent No.: US 7,960,587 B2
(45) Date of Patent: *Jun. 14, 2011

(54) COMPOSITIONS COMPRISING NOVEL COMPOUNDS AND ELECTRONIC DEVICES MADE WITH SUCH COMPOSITIONS

(75) Inventors: Norman Herron, Newark, DE (US); Gary A. Johansson, Hockessin, DE (US); Nora Sabina Radu, Landenberg, PA (US); Eric Maurice Smith, Wilmington, DE (US); Arthur Dabrowski, Herts (GB); Frederick P. Gentry, Bear, DE (US); Gene M. Rossi, Greenville, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1188 days.

This patent is subject to a terminal disclaimer.

(21) Appl. No.: 10/782,357

(22) Filed: Feb. 19, 2004

(65) Prior Publication Data
US 2005/0187411 A1 Aug. 25, 2005

(51) Int. Cl.
C07C 211/00 (2006.01)
H01L 29/08 (2006.01)
H01J 1/62 (2006.01)

(52) U.S. Cl. ........ 564/315; 564/305; 564/307; 428/690; 428/917; 313/504; 313/506; 257/40

(58) Field of Classification Search .................. 428/690, 428/917; 313/504, 506; 257/40; 564/305, 564/433
See application file for complete search history.

(56) References Cited

U.S. PATENT DOCUMENTS

| | | |
|---|---|---|
| 3,265,498 A | 8/1966 | Fox |
| 3,955,978 A | 5/1976 | Rochlitz et al. |
| 4,047,948 A | 9/1977 | Horgan |
| 4,047,949 A | 9/1977 | Horgan |
| 4,115,116 A | 9/1978 | Stolka et al. |
| 4,233,384 A | 11/1980 | Turner et al. |
| 4,265,990 A | 5/1981 | Stolka et al. |
| 4,299,897 A | 11/1981 | Stolka et al. |
| 4,322,487 A | 3/1982 | Merrill et al. |
| 4,346,158 A | 8/1982 | Pai et al. |
| 4,504,564 A | 3/1985 | Pai et al. |
| 4,517,354 A | 5/1985 | D'Alelio |
| 4,665,000 A * | 5/1987 | Tokoli et al. .................... 430/85 |
| 4,714,779 A | 12/1987 | Turner et al. |
| 4,801,517 A | 1/1989 | Frechet et al. |
| 4,933,053 A | 6/1990 | Tieke |

(Continued)

FOREIGN PATENT DOCUMENTS
DE 196 43 097 A1 4/1998

(Continued)

OTHER PUBLICATIONS

Structural data for JP 2000-143786, Nukada et al., Japan.*

(Continued)

*Primary Examiner* — Angela Ortiz
*Assistant Examiner* — Camie Thompson

(57) ABSTRACT

The present invention relates to novel compounds and compositions comprising novel oligomers and polymers, and electronic device comprising at least one layer containing the compositions. The novel oligomers and polymers can be solubilized, and can be used in solution to form electronic devices.

The compounds can function as monomers, and copolymers can be formed from such monomers, such copolymers comprising, as polymerized units, a plurality of units of the compounds.

23 Claims, 1 Drawing Sheet

U.S. PATENT DOCUMENTS

| | | | |
|---|---|---|---|
| 4,933,245 A | 6/1990 | Akasaki et al. | |
| 4,937,165 A | 6/1990 | Ong et al. | |
| 4,946,754 A | 8/1990 | Ong et al. | |
| 5,130,481 A | 7/1992 | Khanna et al. | |
| 5,155,200 A | 10/1992 | Limburg et al. | |
| 5,237,045 A | 8/1993 | Burchill et al. | |
| 5,449,564 A | 9/1995 | Nishio et al. | |
| 5,554,450 A | 9/1996 | Shi et al. | |
| 5,652,067 A | 7/1997 | Ito et al. | |
| 5,681,664 A * | 10/1997 | Tamano et al. | 428/690 |
| 5,789,128 A | 8/1998 | Adachi et al. | |
| 5,792,557 A | 8/1998 | Nakaya et al. | |
| 5,846,681 A | 12/1998 | Yu et al. | |
| 5,891,587 A | 4/1999 | Hu et al. | |
| 5,929,194 A | 7/1999 | Woo et al. | |
| 6,132,913 A | 10/2000 | Fuller et al. | |
| 6,361,885 B1 | 3/2002 | Chou | |
| 6,376,108 B1 | 4/2002 | Otagiri et al. | |
| 6,376,694 B1 | 4/2002 | Uchida et al. | |
| 6,517,957 B1 | 2/2003 | Senoo et al. | |
| 6,646,164 B2 | 11/2003 | Uemura et al. | |
| 6,689,491 B1 | 2/2004 | Nii et al. | |
| 2002/0050597 A1 | 5/2002 | Hirose et al. | |
| 2002/0055014 A1 | 5/2002 | Okada et al. | |
| 2003/0064308 A1 | 4/2003 | Kita et al. | |
| 2003/0207152 A1 | 11/2003 | Hsieh et al. | |
| 2005/0067951 A1* | 3/2005 | Richter et al. | 313/504 |
| 2005/0227465 A1* | 10/2005 | Smith et al. | 438/579 |

FOREIGN PATENT DOCUMENTS

| | | |
|---|---|---|
| DE | 101 09 463 A1 | 10/2002 |
| EP | 0 372 979 A2 | 6/1990 |
| JP | 05-112509 * | 5/1993 |
| JP | 2000-143786 * | 5/2000 |
| JP | 2000297068 A | 10/2000 |
| JP | 2002 212150 A | 7/2002 |
| WO | WO 01/49769 A1 | 7/2001 |
| WO | WO 02/01853 A | 1/2002 |
| WO | WO 2004/005406 A | 1/2004 |

OTHER PUBLICATIONS

Braig, Thomas et al., Crosslinkable hole-transporting polymers by palladium-catalyzed C-N-coupling reaction, Macromol. Rapid Commun., 2000, 583-589, 21(9), Wiley-VCH Verlag GmbH, Weinheim.

Sadighi, Joseph P. et al., Palladium-Catalyzed Synthesis of Monodisperse, Controlled-Length, and Functionalized Oligoanilines.

Nuyken, Oskar et al., Crosslinkable hole- and electron-transport materials for application in organic light emitting devices (OLEDs), Designed Monomers and Polymers, 2002, 195-210, 5(2,3).

Thelakkat, M. et al, "Synthesis and Properties of Novel Hole Transport Materials for Electroluminescent Devices" in Macromolecular Symposia, vol. 125, 1997, pp. 157-164, Wiley VCH, Weinheim, Germany, ISSN 1022-1360.

International Preliminary Report on Patentability, International Bureau of WIPO, Geneva CH, by Agnes Wittmann-Regis, Authorized Officer, on Feb. 28, 2007, in PCT/US2005/05579, the PCT counterpart to the present application.

* cited by examiner

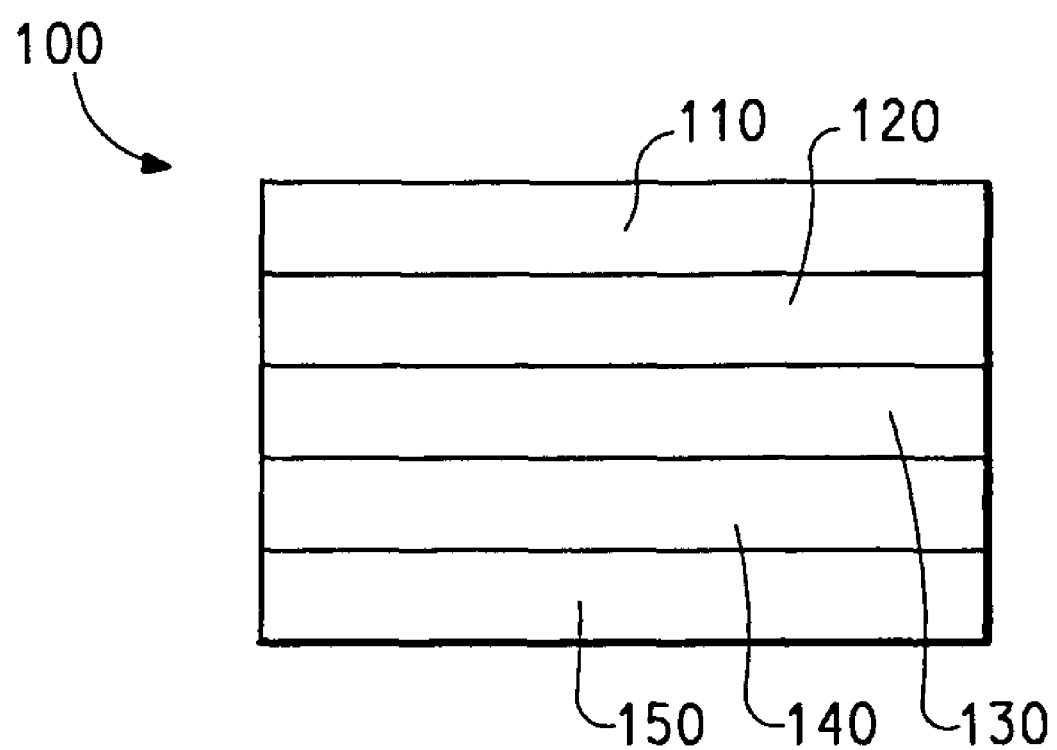
FIG.

COMPOSITIONS COMPRISING NOVEL COMPOUNDS AND ELECTRONIC DEVICES MADE WITH SUCH COMPOSITIONS

BACKGROUND OF THE INVENTION

1. Field of the Invention

The present invention relates to novel compounds useful as hole transport materials in making electronic devices. The invention further relates to electronic devices having at least one active layer comprising such a hole transport material.

2. Background

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices.

SUMMARY OF THE INVENTION

The compounds disclosed herein are useful in making charge transport layers for use in electronic devices. The charge transport layers can be used in any application wherein charge transport capacity is desired. Examples of some uses include, but are not limited to, organic light-emitting diodes ("OLED"s), photovoltaic cells, light sensors, thin film organic transistors, photoconductors, and electrophotographic applications.

One aspect of the invention is a new compound having the formula:

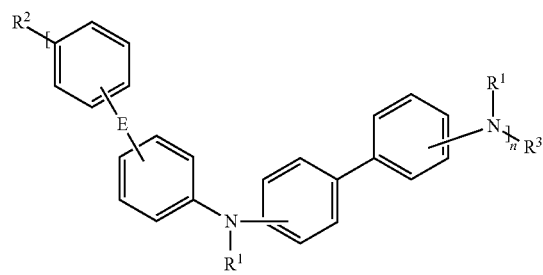

(I)

wherein n is an integer of at least 1 and $R^1$ is selected from aryl, heteroaryl, fluoroaryl, and fluoroheteroaryl substituted with 1 or more fluorine atoms, preferably up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, $R^1$, alkyl, fluoroalkyl, Cl, Br, I and an arylamino group of formula (II),

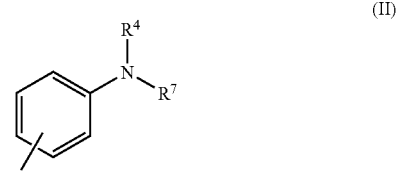

(II)

wherein $R^4$ is selected from aryl, H, $R^1$, alkyl, and fluoroalkyl. Preferably $R^4$ is aryl. $R^7$ is selected from aryl, heteroaryl, fluoroaryl, and fluoroheteroaryl substituted with 1 or more fluorine atoms, preferably up to 7 fluorine atoms.

In some embodiments, $R^2$ is H. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, and E is $(CR^5R^6)_m$, such that when n is greater than 1 and m is 1, at least one of $R^5$ and $R^6$ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form an aromatic or non-aromatic ring. Neighboring aromatic rings can be adjacent or vicinal. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

Another embodiment is a compound of formula

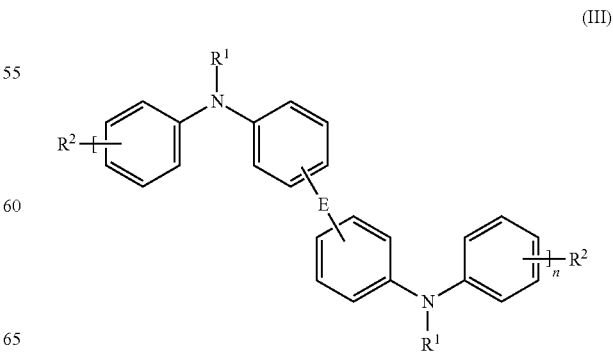

(III)

wherein n is an integer of at least 1, $R^1$ is selected from aryl, heteroaryl, fluoroaryl, and fluoroheteroaryl. preferably, $R^1$ is aryl and may be different at each occurrence (i.e. copolymers). $R^2$ is selected from H, $R^1$, alkyl, fluoroalkyl, arylamino of formula (II), Cl, Br, and I. Preferably, $R^2$ is H or aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, x=0, and $R^2$ is arylamino of formula (II), wherein $R^4$ is selected from aryl, H, $R^1$, alkyl, and fluoroalkyl. Preferably, $R^4$ is aryl.

Another embodiment is a compound of formula

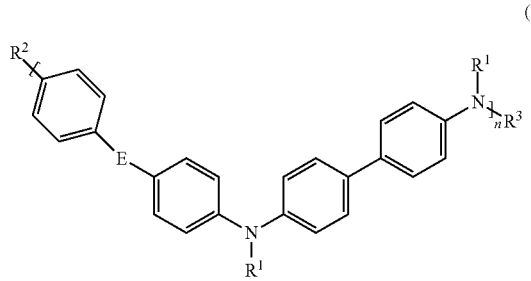

(IV)

wherein:

n is an integer of at least 1, $R^1$ is selected from aryl, heteroaryl, fluoroaryl, and fluoroheteroaryl. and may be different at each occurrence (i.e. copolymers). In some embodiments, $R^1$ is aryl. $R^2$ is selected from H, $R^1$, alkyl, fluoroalkyl, arylamino of formula (II), Cl, Br, I. Preferably, $R^2$ is H. $R^3$ is selected from H and $R^1$. Preferably, $R^3$ is aryl. In some embodiments, $R^2$ is different from $R^3$. In some embodiments, $R^2$ is H and $R^3$ is aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

Another aspect of the present invention is a composition comprising copolymers prepared by copolymerizing multiple functional monomers having the formula (I) or (III) as defined hereinabove, wherein at least one monomer is different from other monomers with which it is copolymerized. The monomers can be copolymerized, for example, using a Pd or Ni catalyzed polymerization procedure.

Another embodiment is an electronic device having at least one layer comprising a compound having the formula:

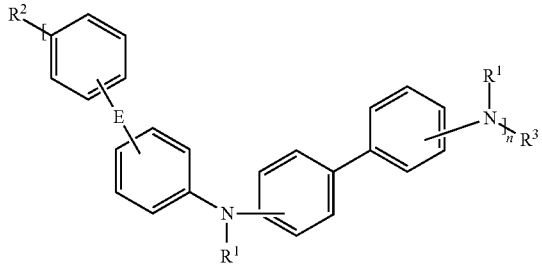

(I)

wherein n is an integer of at least 1 and $R^1$ is selected from aryl, heteroaryl, fluoroaryl, and fluoroheteroaryl substituted with 1 or more fluorine atoms, preferably up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, $R^1$, alkyl, fluoroalkyl, Cl, Br, I and an arylamino group of formula (II),

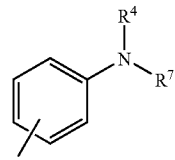

(II)

$R^4$ is selected from aryl, H, $R^1$, alkyl, and fluoroalkyl. Preferably $R^4$ is aryl. $R^7$ is selected from aryl, heteroaryl, fluoroaryl, and fluoroheteroaryl substituted with 1 or more fluorine atoms, preferably up to 7 fluorine atoms.

In some embodiments, $R^2$ is H. In some embodiments, $R^2$ is different from $R^3$. In some embodiments, $R^2$ is H and $R^3$ is aryl. E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

Another aspect of the present invention is an electronic device having at least one layer comprising a compound having the formula

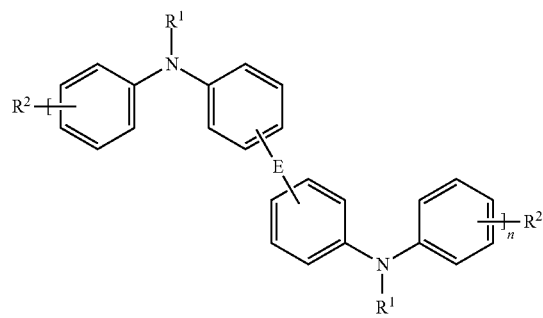

(III)

wherein n is an integer of at least 1, $R^1$ is selected from aryl, heteroaryl, fluoroaryl, and fluoroheteroaryl. preferably, R1 is aryl and may be different at each occurrence (i.e. copolymers). $R^2$ is selected from H, $R^1$, alkyl, fluoroalkyl, arylamino of formula (II), Cl, Br, and I. Preferably, R2 is H or aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^5$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, x=0, and $R^2$ is arylamino of formula (II), wherein $R^4$ is selected from aryl, H, $R^1$, alkyl, and fluoroalkyl. Preferably, $R^4$ is aryl.

Another aspect of the present invention is an electronic device having at least one layer comprising a compound having the formula

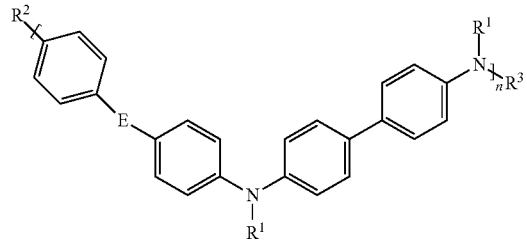

(IV)

wherein:

n is an integer of at least 1, $R^1$ is selected from aryl, heteroaryl, fluoroaryl, and fluoroheteroaryl. and may be different at each occurrence (i.e. copolymers). In some embodiments, $R^1$ is aryl. $R^2$ is selected from H, $R^1$, alkyl, fluoroalkyl, arylamino of formula (II), Cl, Br, I. Preferably, $R^2$ is H. $R^3$ is selected from H and $R^1$. Preferably, $R^3$ is aryl. $R^4$ is selected from aryl, H, $R^1$, alkyl, fluoroalkyl. Preferably $R^4$ is aryl. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

A further aspect of the present invention is a liquid composition comprising a compound having the formula:

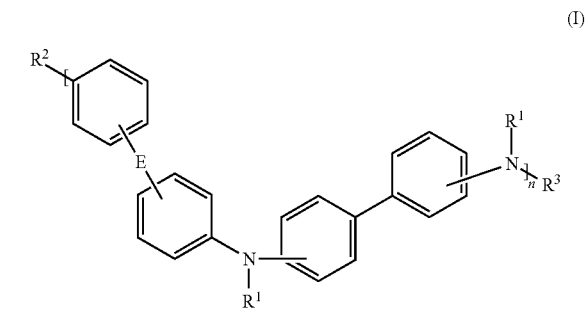

(I)

wherein n is an integer of at least 1 and $R^1$ is selected from aryl, heteroaryl, fluoroaryl, and fluoroheteroaryl substituted with 1 or more fluorine atoms, preferably up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, $R^1$, alkyl, fluoroalkyl, Cl, Br, I and an arylamino group of formula (II),

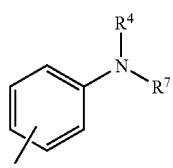

(II)

wherein $R^4$ is selected from aryl, H, $R^1$, alkyl, and fluoroalkyl. Preferably $R^4$ is aryl. $R^7$ is selected from aryl, heteroaryl, fluoroaryl, and fluoroheteroaryl substituted with 1 or more fluorine atoms, preferably up to 7 fluorine atoms.

In some embodiments, $R^2$ is H. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

The liquid composition can be in the form of, for example, a solution or dispersion.

In some embodiments in said liquid, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form and aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

One embodiment, is a liquid composition comprising a compound of formula

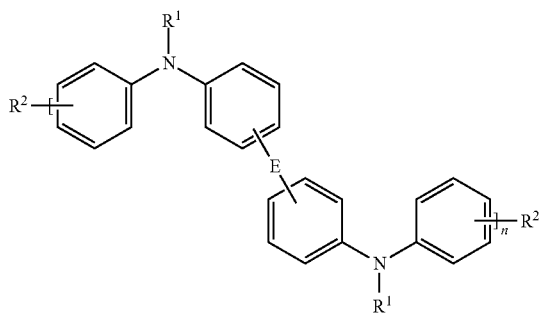

(III)

wherein n is an integer of at least 1, $R^1$ is selected from aryl, heteroaryl, fluoroaryl, and fluoroheteroaryl. preferably, R1 is aryl and may be different at each occurrence (i.e. copolymers). $R^2$ is selected from H, $R^1$, alkyl, fluoroalkyl, arylamino of formula (II), Cl, Br, I. Preferably, R2 is H or aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments in said liquid, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments in said liquid, $R^1$ is selected from phenyl, 1-naphthyl, and 2-naphthyl. In some embodiments, n=1, x=0, and $R^2$ is arylamino of formula (II), wherein $R^4$ is selected from aryl, H, $R^1$, alkyl, and fluoroalkyl. Preferably, $R^4$ is aryl.

Another aspect of the present invention is a liquid comprising a compound of formula

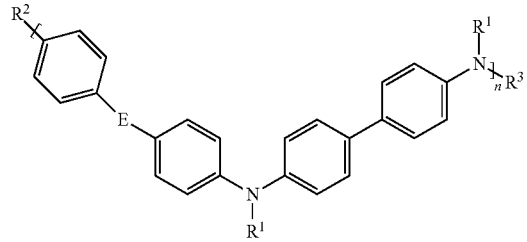

(IV)

wherein n is an integer of at least 1, $R^1$ is selected from aryl, heteroaryl, fluoroaryl, and fluoroheteroaryl and may be different at each occurrence (i.e. copolymers). In some embodiments, $R^1$ is aryl. $R^2$ is selected from H, $R^1$, alkyl, fluoroalkyl, arylamino of formula (II), Cl, Br, I. Preferably, $R^2$ is H. $R^3$ is selected from H and $R^1$. Preferably, $R^3$ is aryl. $R^4$ is selected from aryl, H, $R^1$, alkyl, fluoroalkyl. Preferably $R^4$ is aryl. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments in said liquid, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

A further aspect of the present invention is an electronic device comprising a compound having the formula:

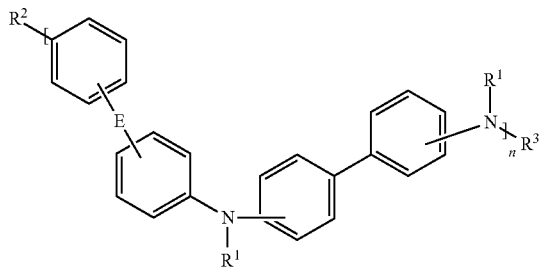

(I)

wherein n is an integer of at least 1 and $R^1$ is selected from aryl, heteroaryl, fluoroaryl, and fluoroheteroaryl substituted with 1 or more fluorine atoms, preferably up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, $R^1$, alkyl, fluoroalkyl, Cl, Br, I and an arylamino group of formula (II),

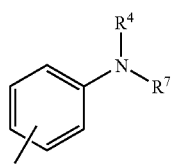

(II)

$R^4$ is selected from aryl, H, $R^1$, alkyl, and fluoroalkyl. Preferably $R^4$ is aryl. $R^7$ is selected from aryl, heteroaryl, fluoroaryl, and fluoroheteroaryl substituted with 1 or more fluorine atoms, preferably up to 7 fluorine atoms.

In some embodiments, $R^2$ is H. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments in said device, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form an aromatic or non-aromatic ring. In further embodiments, two adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

Another aspect of the present invention is an electronic device comprising a compound of formula

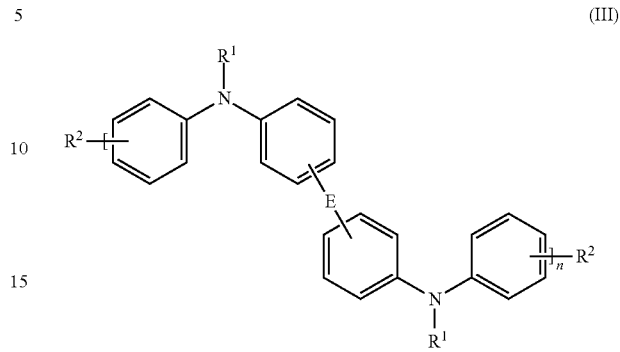

(III)

wherein n is an integer of at least 1, $R^1$ is selected from aryl, heteroaryl, fluoroaryl, and fluoroheteroaryl. preferably, R1 is aryl and may be different at each occurrence (i.e. copolymers). $R^2$ is selected from H, $R^1$, alkyl, fluoroalkyl, arylamino of formula (II), Cl, Br, I. Preferably, R2 is H or aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments in said device, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments in said device, $R^1$ is selected from phenyl, 1-naphthyl, and 2-naphthyl. In some embodiments, n=1, x=0, and $R^2$ is arylamino of formula (II), wherein $R^4$ is selected from aryl, H, $R^1$, alkyl, and fluoroalkyl. Preferably, $R^4$ is aryl.

Another aspect of the present invention is an electronic device comprising a compound of formula

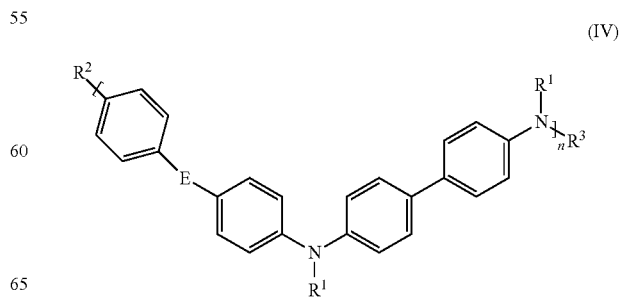

(IV)

wherein n is an integer of at least 1, R¹ is selected from aryl, heteroaryl, fluoroaryl, and fluoroheteroaryl, and may be different at each occurrence (i.e. copolymers). In some embodiments, R¹ is aryl. R² is selected from H, R¹, alkyl, fluoroalkyl, arylamino of formula (II), Cl, Br, I. Preferably, R² is H. R³ is selected from H and R¹. Preferably, R³ is aryl. R⁴ is selected from aryl, H, R¹, alkyl, fluoroalkyl. Preferably R⁴ is aryl. In some embodiments, R² is different from R³. In some embodiments, R² is H and R³ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein R⁵ and R⁶ are each independently selected from H, F, alkyl, aryl, alkoxy, aryloxy, fluoroalkyl, fluoroaryl, fluoroalkoxy, and fluoroaryloxy and wherein R⁵ and R⁶ can, when taken together, form a non-aromatic ring, provided that when E is $(CR^5R^6)_m$, and n is greater than 1 and m is 1, at least one of R⁵ and R⁶ is not hydrogen or a hydrocarbon.

In some embodiments in said device, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, R¹ is selected from phenyl, 1-naphthyl, and 2-naphthyl. In some embodiments, n=1, R² is H, and R³ is selected from phenyl, 1-naphthyl, and 2-naphthyl.

A further aspect of the present invention is a process for making an electronic device. The process includes: providing a liquid comprising a compound having the formula (I) as described hereinabove; providing an anode; contacting said liquid comprising said compound with said anode; Removing said liquid from said compound to produce a hole transport film; providing an emitter; disposing said emitter adjacent to said hole transport film; providing an electron transporter and disposing said electron transporter adjacent to said emitter; and providing a cathode adjacent to said electron transporter. The liquid can be, for example, a solution or dispersion.

The foregoing general description and the following detailed description are exemplary and explanatory only and are not restrictive of the invention, as defined in the appended claims.

DESCRIPTION OF THE DRAWINGS

The invention is illustrated by way of example and not limitation in the accompanying figures.

FIG. 1: An illustrative example of one organic electronic device comprising at least one layer comprising a novel compound as disclosed herein.

DETAILED DESCRIPTION OF THE EMBODIMENTS

The present invention provides novel compounds, novel methods of making said compounds, compositions and devices containing the compounds, and methods for making devices containing the compounds. One aspect of the present invention is a composition comprising a compound having the formula:

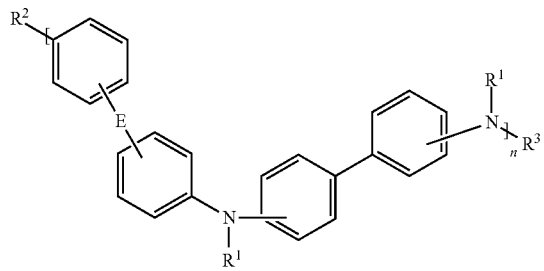

(I)

wherein n is an integer of at least 1 and R¹ is selected from aryl, heteroaryl, fluoroaryl, and fluoroheteroaryl substituted with 1 or more fluorine atoms, preferably up to 7 fluorine atoms. The compound comprises more than one group R¹, and R¹ can be different at each occurrence. For example, the compound represented by formula (I) can function as a monomer, and copolymers can be formed from the compound, such copolymers comprising, as polymerized units, a plurality of units having formula (I) in which at least one unit contains R¹ different from R¹ in other units. In some embodiments, R¹ is aryl.

R³ is selected from H and R¹. R² is selected from H, R¹, alkyl, fluoroalkyl, Cl, Br, I and an arylamino group of formula (II),

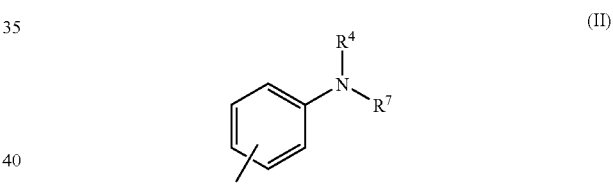

(II)

R⁴ is selected from aryl, H, R¹, alkyl, and fluoroalkyl. Preferably R⁴ is aryl. R⁷ is selected from aryl, heteroaryl, fluoroaryl, and fluoroheteroaryl substituted with 1 or more fluorine atoms, preferably up to 7 fluorine atoms.

In some embodiments, R² is H. In some embodiments, R² is different from R³. In some embodiments, R² is H and R³ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein R⁵ and R⁶ are each independently selected from H, F, alkyl, aryl, alkoxy, aryloxy, fluoroalkyl, fluoroaryl, fluoroalkoxy, and fluoroaryloxy and wherein R⁵ and R⁶ can, when taken together, form a non-aromatic ring, provided that when E is $(CR^5R^6)_m$, and n is greater than 1 and m is 1, at least one of R⁵ and R⁶ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

In one embodiment, is a composition comprising a compound of formula

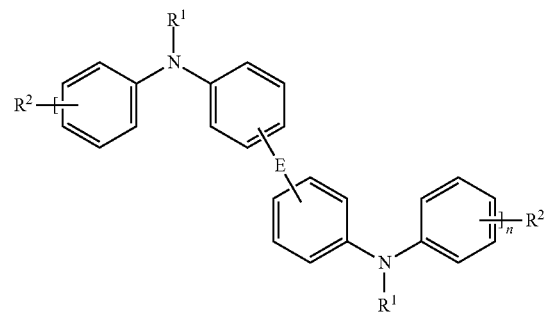

(III)

wherein n is an integer of at least 1, $R^1$ is selected from aryl, heteroaryl, fluoroaryl, and fluoroheteroaryl. preferably, R1 is aryl and may be different at each occurrence (i.e. copolymers). $R^2$ is selected from H, $R^1$, alkyl, fluoroalkyl, arylamino of formula (II), Cl, Br, I. Preferably, R2 is H or aryl. $R^4$ is selected from aryl, H, $R^1$, alkyl, fluoroalkyl. Preferably $R^4$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, x=0, and $R^2$ is arylamino of formula (II), wherein $R^4$ is selected from aryl, H, $R^1$, alkyl, and fluoroalkyl. Preferably, $R^4$ is aryl.

Another aspect, in one embodiment, is a new composition comprising a compound of formula

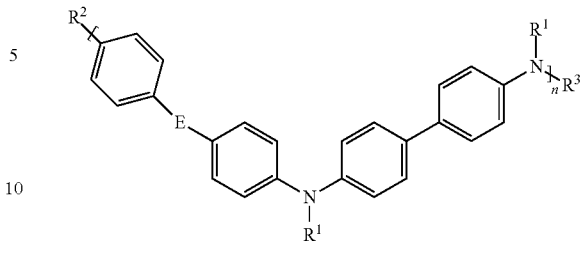

(IV)

wherein n is an integer of at least 1, $R^1$ is selected from aryl, heteroaryl, fluoroaryl, and fluoroheteroaryl, and may be different at each occurrence (i.e. copolymers). In some embodiments, $R^1$ is aryl. $R^2$ is selected from H, $R^1$, alkyl, fluoroalkyl, arylamino of formula (II), Cl, Br, I. Preferably, $R^2$ is H. $R^3$ is selected from H and $R^1$. Preferably, $R^3$ is aryl. $R^4$ is selected from aryl, H, $R^1$, alkyl, fluoroalkyl. Preferably $R^4$ is aryl. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

The practical upper limit of n in formulas (I), (III) and (IV) is determined in part by the desired solubility of a compound in a particular solvent or class of solvents. As the value of n increases, the molecular weight of the compound increases. The increase in molecular weight is generally expected to result in a reduced solubility of the compound in a particular solvent. Moreover, in one embodiment, the value of n at which a compound becomes substantially insoluble in a given solvent is dependent in part upon the structure of the compound. For example, a compound containing multiple phenyl groups may become substantially insoluble in an organic solvent when n is much less than about $10^4$. As another example, a compound containing fewer phenyl groups and/or phenyl groups with particular functional groups may be soluble in a given solvent even though n is about $10^4$ or greater, even $10^5$ or $10^6$. The selection of the value of n and a solvent is within the purview of one skilled in the art.

Also provided are compositions comprising novel copolymers prepared by combining multiple functional monomers. The monomers are units of compounds disclosed herein, which can be polymerized to form the novel copolymers. The monomers can be copolymerized, for example, using a Pd or Ni catalyzed polymerization procedure. Such monomers can be grouped into three classes as follows:

Group 1
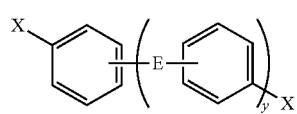 A1
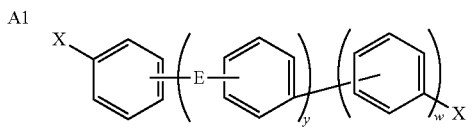 A2
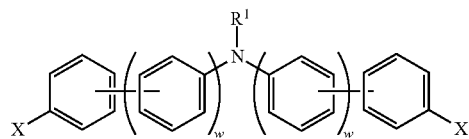 B
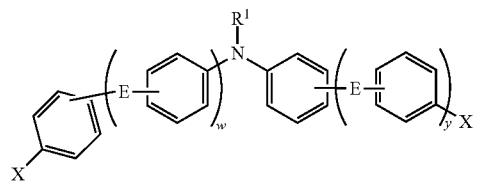 C1
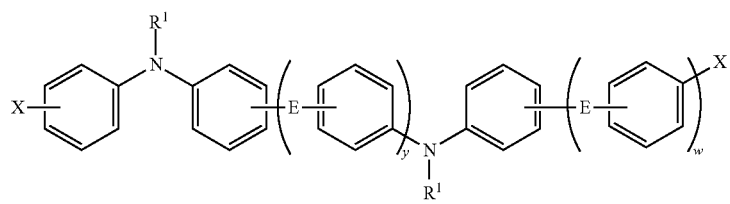 C2
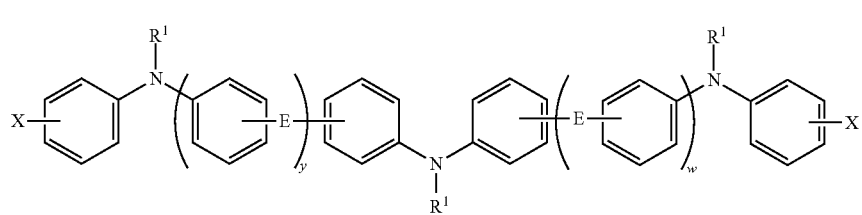 C3
Group 2
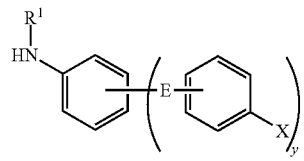 D1
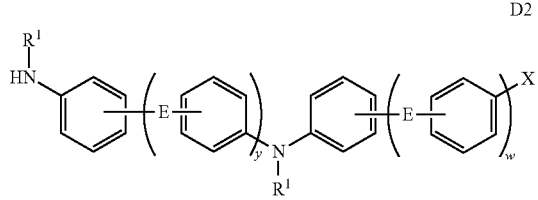 D2
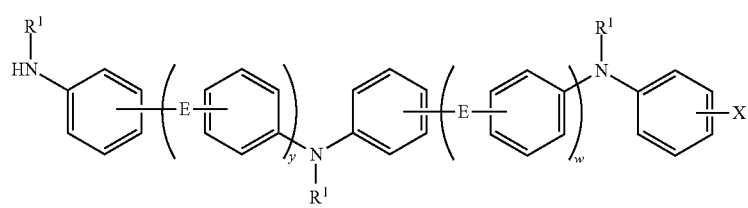 D3
Group 3
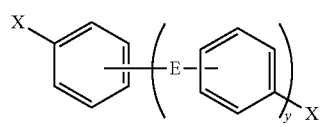 A1
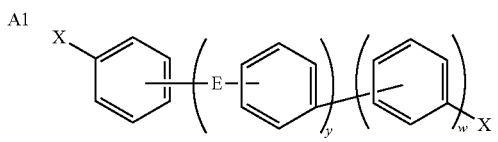 A2

-continued

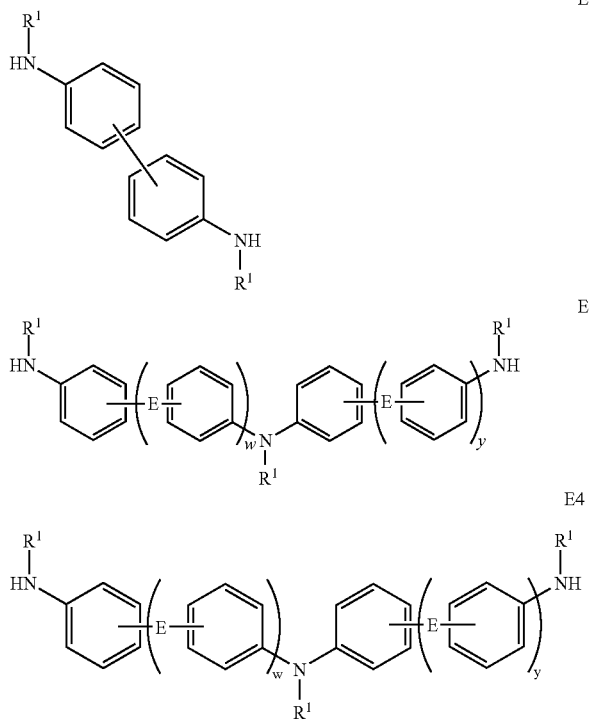

E1

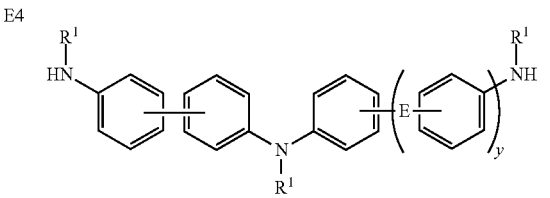

E2

E4

E5

E4

Where y is an integer equal or greater than 1 and w is zero or an integer equal or greater than one, and X is Cl, Br, I, boronic acid, boronic acid ester, boranes or a triflate group; and wherein X can be different at each occurrence such that carbon-carbon (for Group 1) and carbon-nitrogen bonds (for Groups 2 and 3) can be formed.

For convenience, exemplary monomers are assigned herein to Group 1, Group 2 or Group 3, and within the Groups, exemplary monomers are assigned to Subgroups such as, for example, within Group 1, subgroups A1, A2, B, C1, C2, and C3.

Copolymers can be made using one or more monomers from each of subgroups within each of Group 1, Group 2, and/or Group 3, provided that no copolymers containing only monomers from subgroups A or copolymers containing only monomers from subgroup B are obtained. Copolymers made from monomers within Group 3 contain at least one comonomer designated A1 or A2, and at least one comonomer from subgroup E1, E2, E3, E4 and E5. Exemplary copolymers include poly(A-co-B); poly(A-co-C); poly(A-co-B-co-C); poly(A-co-C); and copolymers comprising two or more monomers within group C, wherein, for example, "poly(A-co-B)" refers to a copolymer comprising, as polymerized units, monomers in Group A and monomers in Group B. The monomers, e.g., A and B, in such copolymers, can be present in equimolar ratios or in non-equimolar ratios. Copolymers made from monomers in Group 1 are made by formation of carbon-carbon bonds during polymerization. Copolymers made from monomers in Groups 2 and Groups 3 are made by formation of carbon-nitrogen bonds during polymerization.

The copolymers from Group 1 can generally be prepared using known synthetic methods. In one synthetic method, as described in Yamamoto, *Progress in Polymer Science*, Vol. 17, p 1153 (1992), the dihalo derivatives of the monomeric units are reacted with a stoichiometric amount of a zerovalent nickel compound, such as bis(1,5-cyclooctadiene)nickel(0). In another method, as described in Colon et al., *Journal of Polymer Science*, Part A, Polymer chemistry, Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

For example, homopolymers or copolymers containing monomers from Group 2 can be formed by reacting a monomer unit having a reactive primary or secondary amine and a reactive aryl halide in the presence of cupper, nickel or palladium catalysts. Homopolymers or copolymers containing monomers from Group 3 can be produced by the reaction of one or more dihalo monomeric derivative(s) with one or more diamino (primary or secondary) monomeric unit(s) in the presence of cupper, nickel or palladium catalysts. Typical conditions for Pd-catalyzed amination reactions are described in Sadighi, J. P.; Singer, R. A.; Buchwald, S. L. *J. Am. Chem. Soc.* 1998, 120, 4960; Wolfe, J. P.; Tomori, H.; Sadighi, J. P.; Yin, J.; Buchwald, S. L. J., *Org. Chem.* 200, 65, 1158; Hartwig, J. F.; *Modern Arene Chemistry* 2002, 107-168, Astruc, D., Editor, Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedron,* 2001, 57, 6054.; Wolfe, J. P.; Buchwald, S. L., *J. Am. Chem. Soc.* 1997, 119, 4960. Typical conditions for Cu-catalyzed amination reactions are described in Klapars, A.; Antilla, J. C.; Huang, X.; Buchwald, S. L., *J. Am. Chem. Soc.* 2001, 123, 7727.

Oligomers, including dimers, and polymers of the compounds disclosed herein have improved thermal stability in comparison to, e.g., NPD and TPD. For example, a compound of Formula IV wherein $R^1$ is 1-naphthyl and E is $C(CF_3)_2$ preferably has a $T_g$ of about 240° C. Typically, the compounds have a $T_g$ of at least about 50° C., preferably at least about 100° C.

Compositions of formulas I and IV can be prepared via carbon-nitrogen bond formation methods known to one skilled in the art. For example, homo- or hetero-polymers can be produced by the reaction of one or more dihalo monomeric derivative(s) with equimolar amounts of one or more diamino (primary or secondary) monomeric unit(s) in the presence of copper, nickel or palladium catalysts. Alternatively, one or more monomers containing an amine and a halide as reactive groups can be employed. Typical conditions for Pd-catalyzed amination reactions are described in Sadighi, J. P.; Singer, R. A.; Buchwald, S. L. *J. Am. Chem. Soc.* 1998, 120, 4960.; Wolfe, J. P.; Tomori, H.; Sadighi, J. P.; Yin, J.; Buchwald, S. L. *J. Org. Chem.* 200, 65, 1158.; Hartwig, J. F. *Modern Arene Chemistry* 2002, 107-168. Editor: Astruc, D., Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedon,* 2001, 57, 6054.; Wolfe, J. P.; Buchwald, S. L. J. Am. Chem. Soc. 1997, 119, 4960. Typical conditions for Cu-catalyzed amination reactions are described in Klapars, A.; Antilla, J. C.; Huang, X.; Buchwald, S. L. *J. Am. Chem. Soc.* 2001, 123, 7727.

For example, a diamine monomer E1 from Group 3, such as N,N'-diphenylbenzidine, is reacted with an equimolar amount of a dihalide monomer A1, such as 4,4'-bromophenylisopropylidene, in presence of a suitable base, such as NaO'Bu, catalytic (less than one equivalent) amount of a suitable palladium compound, such as tris(dibenzylideneacetone)dipalladium, and a suitable ligand, such as P($^t$Bu)$_3$. The polymerization is conducted at a temperature between 22° C. to 150° C. for 24 to 92 hours. The resulting polymer is then treated with an endcapping group, such as bromobenzene, and allowed to further react for another 24 to 48 hours to produce a polymer of formula IV, where $R^1$ is phenyl, E is $C(CH_3)_2$ and $R^2$=$R^3$ is phenyl.

In another example, monomer D1 from Group 2, such as 4-(N-phenylamine)$_4$'-(bromophenyl)isopropylidene, can be polymerized using conditions described above to give a polymer of formula IV, where $R^1$ is phenyl, E is $C(CH_3)_2$ and $R^2$=$R^3$ is phenyl.

Compounds of formula III can be prepared via carbon-carbon bond formation methods known to one skilled in the art. In one method, described in Yamamoto, Progress in Polymer Science, Vol. 17, p 1153 (1992), the dihalo derivatives of the monomeric units are reacted with a stoichiometric amount of a zerovalent nickel compound, such as bis(1,5-cyclooctadiene)nickel(0). In the second method, as described in Colon et al., Journal of Polymer Science, Part A, Polymer chemistry Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

For example, a polymeric composition of monomer C2 from Group 1, such as 4,4'-N,N'-[(1-naphthyl)(4-chlorophenyl)]-(hexaflouroisopropylidene) is reacted with a stoichiometric amount of a zerovalent nickel compound, such as bis(1,5-cyclooctadiene)nickel(0), at a temperature between 22° C. to 150° C. for 24 to 92 hours.

For making electronic devices, including OLED devices, in one embodiment, the compounds form films when deposited onto a transparent anode such as indium-doped tin oxide (ITO). The quality of the resultant film can be superficially judged by visual/microscopic inspection for smoothness and defect density. With respect to OLEDs, it is preferred that visually observed defects be minimal. Furthermore, film quality can be measured by estimation of film thickness over several separate areas of the film using, for example, an optical ellipsometer or a mechanical profilometer; it is preferred that the films have substantially uniform thicknesses as measured in the different areas of the film.

The compounds can be used in liquid form, such as a dispersion or solution, in making electronic devices. An exemplary process for making an electronic device includes: providing a liquid comprising a compound having the formula (I) as described hereinabove; providing an anode; contacting said liquid comprising said compound with said anode; Removing said liquid from said compound to produce a hole transport film; providing an emitter; disposing said emitter adjacent to said hole transport film; providing an electron transporter and disposing said electron transporter adjacent to said emitter; and providing a cathode adjacent to said electron transporter.

The liquid is preferably a solvent for the compound. A preferred solvent for a particular compound or related class of compounds can be readily determined by one skilled in the art. For some applications, it is preferred that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics.

Other suitable liquids for use in making the liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes, including triflurotoluene), polar solvents (such as tetrahydrofuran (THP), N-methylpyrrolidone)esters (such as ethylacetate) alcohols (isopropanol), keytones (cyclopentatone) and mixtures thereof.

The compounds disclosed herein are triarylamine derivatives, and can be in the form of dimers, oligomers or polymers, particularly dimers. The compounds can provide the electronic advantages of smaller molecules such as triarylamines, with the solution processability, film forming capabilities, solubility properties, and thermal stability of polymeric compounds. In particular, it has been found that the compounds can be provided in solution and used in solution processes to manufacture electronic devices.

In one embodiment, the electronic devices for which the compounds are useful are OLED devices. In contrast to known compounds such as NPD (N,N'-di(naphthalen-1-yl)-N,N'-diphenyl-benzidine) and TPD (4,4'-bis[N-(3-methylphenyl)-N-phenylamino]biphenyl), which are commonly used as hole transport materials in making OLED devices, using vapor deposition processes, the present compounds have improved thermal stability and can be selectively solubilized in common solvents. By selectively solubilized is meant that the compounds can be made to be soluble or substantially soluble in some solvents and insoluble or substantially insoluble in other solvents. For example, in using the compounds to make electronic devices it is often desirable to provide the compound in a solvent in which the compound is soluble or substantially soluble, and deposit thereon another solvent in which the compound is insoluble or substantially insoluble. Solubilization can be provided or enhanced by variation of substituent groups on the compounds.

In one embodiment, the compound is dissolved in a solvent in which the compound is substantially soluble. The solution is then formed into a thin film and dried by any of several techniques such as spin-depositing, inkjetting etc. The resultant film formed as the solvent evaporates is then further dried by baking at elevated temperatures, including above the boiling point of the solvent, either in a vacuum of nitrogen atmosphere. The film is then subjected to further processing by depositing a second solution containing emissive layer materials on top of the pre-formed compound film where the emissive materials are dissolved in a solvent in which the compound is substantially insoluble. By "substantially insoluble" is meant that less than about 5 mg of the compound dissolves in 1 ml of the solvent. However, solubilities greater than or less than 5 mg can be used and may be preferred for some applications. For example, a modest solubility up to 10 mg/mL may result in a blurred or graded interface between the HTM polymer of the present invention and the emissive layer materials. Such blurring can have deleterious or beneficial effects depending upon the natures of the materials involved. Such blurring of the interface can result in improved charge transport across the interface and substantially improved device performance or lifetime.

As will be recognized by one skilled in the art, the solubility of a compound is determined in part by substituent groups within the compound. In particular, in the compounds disclosed herein, the nature of the group "E" in the compound can be varied in order to control the solubility of a compound in a particular solvent or class of solvents. Thus, by varying the nature of the group "E", a compound can be modified such that is more or less soluble in water or any given organic non-aqueous solvent.

Also preferably, for making electronic devices, the compounds have a relatively low solubility, e.g., a solubility less than about 5 mg/mL, even about 2 mg/mL or less, in solvents that can be used to deposit an emissive layer layer film onto an electrode, which is typically a transparent anode such as ITO (indium doped tin oxide).

The present invention also relates to electronic devices comprising at least one layer containing a composition as disclosed herein, as a hole transport layer. The compositions can be in a separate layer, positioned between a photoactive layer and an electrode. Alternatively, a photoactive layer of an organic electronic device can contain the composition. An example of an electronic device that can contain a composition as disclosed herein is shown in Figure X. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. In the illustrated embodiment, the device has an optional additional transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary,* 470 and 476 (McGraw-Hill, Inc. 1966).

The compounds disclosed herein are particularly useful in the hole transport layer 120, and as a charge conducting host in the photoactive layer, 130. The other layers in the device can be made of any materials that are known to be useful in such layers. The anode, 110, is an electrode that is particularly efficient for injecting positive charge carriers. It can be made of, for example, materials containing a metal, mixed metal, alloy, metal oxide or mixed-metal oxide, a conducting polymer, or a combination or mixture thereof. Suitable metals include the Group 11 metals, the metals in Groups 4, 5, and 6, and the Group 8-10 transition metals. If the anode is to be light-transmitting, mixed-metal oxides of Group 12, 13 and 14 metals, such as indium-tin-oxide, are generally used. The anode 110 can also comprise an organic material such as polyaniline, as described, for example, in "Flexible light-emitting diodes made from soluble conducting polymer," *Nature* vol. 357, pp 477-479 (11 Jun. 1992). At least one of the anode and cathode is preferably at least partially transparent to allow the generated light to be observed.

Examples of the photoactive layer 130 include all known electroluminescent materials, including fluorescing and phosphorescing materials (including both organo-metallic complexes and conjugated polymers). Organometallic electroluminescent compounds are preferred. The most preferred compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications U.S. 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. Examples of a few suitable iridium complexes are given in FIG. 6, as Formulae IV(a) through IV(e). Analogous tetradentate platinum complexes can also be used. These electroluminescent complexes can be used alone, or doped into charge-carrying hosts, as noted above. The compounds, in addition to being useful in the hole transport layer 120, electronic transport layer 140/150 can also act as a charge carrying host for an emissive dopant in the photoactive layer 130 or otherwise part of the photoactive layer.

Examples of electron transport materials which can be used in layer 140 and/or layer 150 include metal chelated oxinoid compounds, such as tris(8-hydroxyquinolato)aluminum (Alq$_3$); and azole compounds such as 2-(4-biphenylyl)-

5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

Examples of other organic electronic devices that may benefit from having one or more layers comprising the new compounds and compositions described herein include: (1) devices that convert electrical energy into radiation (e.g., a light-emitting diode, light emitting diode display, or diode laser), (2) devices that detect signals through electronics processes (e.g., photodectors, photoconductive cells, photoresistors, photoswitches, phototransistors, phototubes), IR detectors, (3) devices that convert radiation into electrical energy, (e.g., a photovoltaic device or solar cell), and (4) devices that include one or more electronic components that include one or more organic semi-conductor layers (e.g., a transistor or diode).

It is understood that each functional layer may be made up of more than one layer.

The devices can be prepared using a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied from solutions or dispersions in suitable solvents, using any conventional coating or printing technique, including but not limited to spin-coating, dip-coating, roll-to-roll techniques, ink-jet printing, screen-printing, gravure printing and the like. Combinations of vapor deposition and solution coating of individual layers can be used. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layer 140 and 150, 50-2000 Å, preferably 100-1000 Å; cathode 160, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

As used herein, the term "charge transport composition" is intended to mean material that can receive a charge from an electrode and facilitate its movement through the thickness of the material with relatively high efficiency and small loss of charge. Hole transport compositions are capable of receiving a positive charge from an anode and transporting it. Electron transport compositions are capable of receiving a negative charge from a cathode and transporting it.

The term "composition", used alone to refer to compositions having particular formulas disclosed and claimed herein, is intended to be construed broadly to include the compounds, monomers, dimers, oligomers and polymers thereof, as well as solutions, dispersions, liquid and solid mixtures and admixtures.

The term "anti-quenching composition" is intended to mean a material which prevents, retards, or diminishes both the transfer of energy and the transfer of an electron to or from the excited state of the photoactive layer to an adjacent layer.

The term "photoactive" refers to any material that exhibits electroluminescence, photoluminescence, and/or photosensitivity.

The term "group" is intended to mean a part of a compound, such as a substituent in an organic compound. The prefix "hetero" indicates that one or more carbon atoms have been replaced with a different atom.

The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted.

The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment.

The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted.

The terms "heteroalkenyl", "heteroalkenylene", "heteroalkynyl" and "heteroalkynylene" are intended to mean analogous groups having one or more heteroatoms.

The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted.

The term "arylalkylene" is intended to mean a group derived from an alkyl group having an aryl substituent, which group may be further unsubstituted or substituted. The term "heteroarylalkylene" is intended to mean a group derived from an alkyl group having a heteroaryl substituent, which group may be further unsubstituted or substituted.

The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted.

The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom.

Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "compound" is intended to mean an electrically uncharged substance made up of molecules that further consist of atoms, wherein the atoms cannot be separated by physical means.

The term "polymeric" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, 81$^{st}$ Edition, 2000).

As used herein, "solution processing" means processes that include depositing from a liquid medium. The liquid medium can be in the form of a solution, a dispersion, an emulsion, or other forms.

The term "layer" or "film" refers to a coating covering a desired area. The area can be as large as an entire display, or as small as a specific function area such as a single sub-pixel. Films can be formed by any conventional deposition technique. Typical liquid deposition techniques include, but are not limited to, continuous deposition techniques such as spin coating, gravure coating, curtain coating, dip coating, slot-die coating, spray-coating, and continuous nozzle coating; and discontinuous liquid deposition techniques such as ink jet printing, gravure printing, and screen printing.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "the", "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

Example 1

Polymer Obtained from Monomer 1

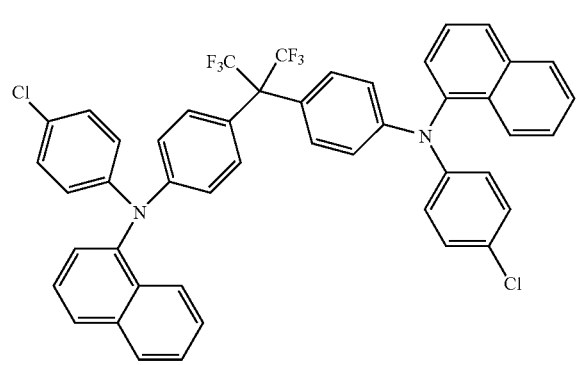

Synthesis of Monomer 1
Synthetic pathway to compound 1 is shown below.

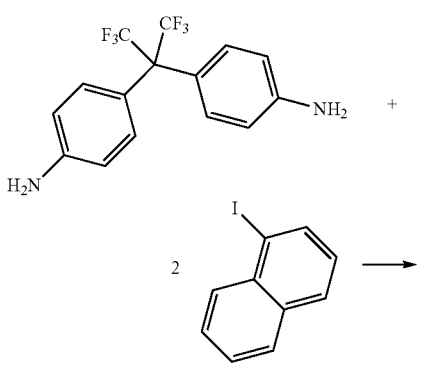

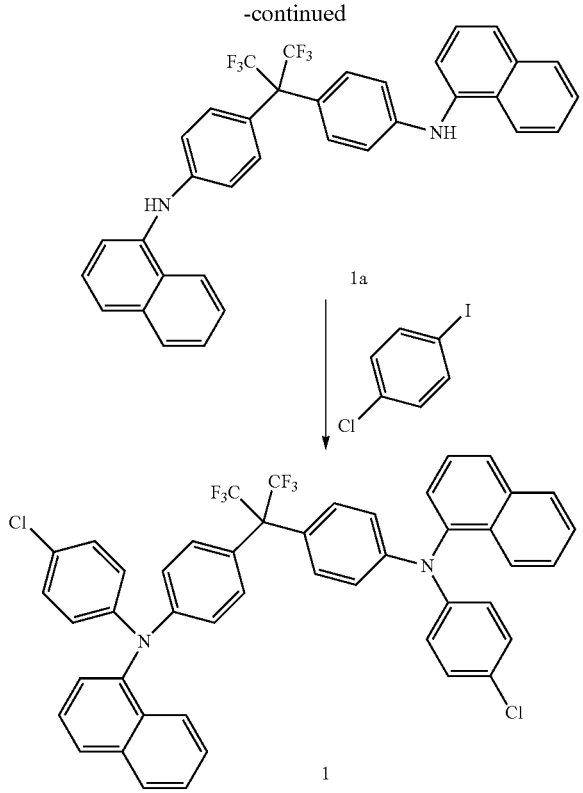

All reactions were performed under a nitrogen atmosphere and the reaction flask was kept away from room light. To a toluene (anhydrous, 300 mL) solution of 4,4'-(hexaflouroisopropylidene)dianiline (15.0 g), 1-iodonaphthalene (22.9 g) and NaOtBu (12.95 g), a mixture of tris(dibenzylideneacetone)dipalladium (4.12 g) and P$^t$Bu$_3$ (2.28 g) was added. The resulting reaction mixture was stirred at room temperature for five days, after which it was filtered through a plug of celite and washed with toluene (3×500 mL). The volatiles were removed by rotorary evaporation and the product was purified by column chromatography (silica) using EtOAc/hexane (1:5) followed by crystallization from CH$_2$Cl$_2$/hexane to yield 1a in 67% yield (17.6 g).

A toluene (anhydrous, 480 mL) solution of 1a (17.6 g) was then mixed with 1-chloro-4-iodobenzene (28.6 g), NaOtBu (8.65 g), tris(dibenzylideneacetone)dipalladium (2.20 g) and 1,1'-bis(diphenyphosphino)ferrocene (2.66 g). The resulting reaction mixture was heated to 100 C. for 48 hrs, after which it was filtered through a plug of celite and washed with toluene (4×250 mL). The volatiles were removed and the product was purified by column chromatography (silica) using 1 L hexane followed by 15% CH$_2$Cl$_2$/hexane to give 1 as a white powder in 64% (15.4 g) yield.

Polymerization of 1

Bis(1,5-Cyclooctadiene)-nickel-(0) (3.334 g, 12.12 mmol) was added to a N,N-dimethylformamide (anhydrous, 15 mL) solution 2,2'-bipyridyl (1.893 g, 12.12 mmol) and 1,5-cyclooctadiene (1.311 g, 12.12 mmol). The resulting mixture was heated to 60 C. for 30 min. The oil bath temperature was then raised to 70 C. and a toluene (anhydrous, 60 mL) solution of 1 (4.846 g 6.0 mmol) was added rapidly to the stirring catalyst mixture. The mixture was stirred at 70 C. for 92 hours. After the reaction mixture cooled to room temperature, it was poured, slowly, with vigorous stirring into 600 mL of an acetone/methanol (50:50 by volume) mixture containing ~30 mL conc. HCl. A light-gray fiberous precipitate formed which partially broke-up during stirring. The mixture was stirred for one hour and the solid was isolated by filtration. The solid was dissolved in ~200 mL of chloroform and was poured with vigorous stirring, into 1200 mL of an acetone/methanol (50:50) mixture containing ~30 mL conc. HCl. A light-gray fiberous mass formed, which was stirred for one hour and isolated by filtration. The solid was again dissolved in ~200 mL chloroform, passed through a bed (~3-4 cm) of silica gel 60. The filter bed was rinsed with ~400 mL chloroform and the combined chloroform solutions were concentrated to ~150-200 mL and poured, with vigorous stirring into 1600 mL of acetone/methanol (50:50 by volume). A slightly off-white fiberous precipitate formed, which stirred for one hour. The solid was isolated by filtration and was dried under vacuum overnight. The solid was dissolved in tetrahydrofuran (250 mL) and then slowly poured with vigorous stirring into 1500 mL of ethyl acetate. The polymer precipitated out as a slightly off-white fiberous slurry. After stirring this mixture for one hour the precipirate was isolated by filtration. This solid was re-dissolved on more time in tetrahydrofuran (220 mL), filtered through a 0.2 um syringe filter (PTFE filter membrane) and poured, slowly, with vigorous stirring into 1200 mL of methanol. The polymer precipitated out as a white fiberous slurry, which was isolated by filtration. After drying the resulting material under vacuum overnight 3.31 g (75%) of polymer was isolated. GPC (THF, room temperature): Mn=92,000; Mw=219,900; Mw/Mn=2.39.

Example 2

Synthesis of Polymer 2

Synthetic pathway to polymer 2 is shown below.

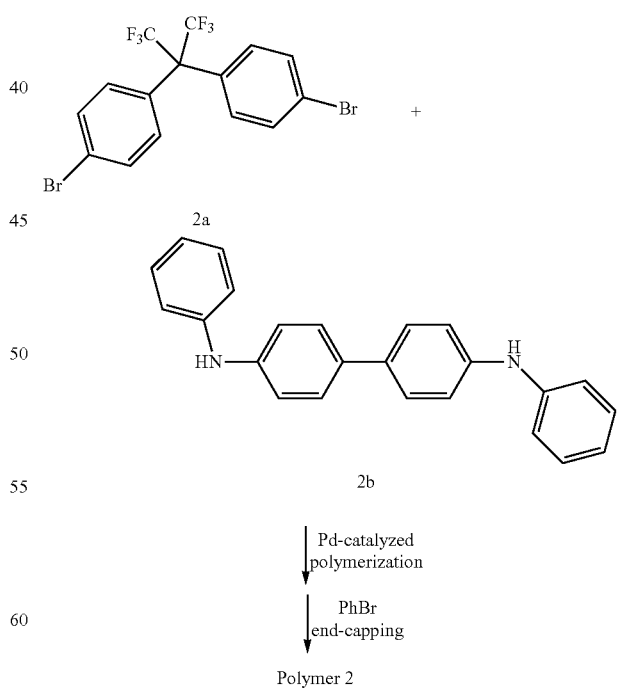

All manipulations were performed under an atmosphere of nitrogen. A 200 mL flask was charged with 4,4'-bromophenyl (hexaflouroisopropylidene) (3.64 g, 7.87 mmol), N,N-diphenylbezidine (2.67, 7.93 mmol), NaO'Bu (2.29, 23.8 mmol), toluene (anhydrous, 95 mL), and a solution (10 mL, toluene) of tris(dibenzylideneacetone)dipalladium (0.363 g, 0.4 mmol) and P'Bu₃ (0.482 g, 2.4 mmol). The resulting reaction mixture was heated to 100° C. for 48 hrs. Bromobenzene (2.74 g, 17.4 mmol) was added to the reaction mixture and allowed to stir for an additional 24 hours. After cooling to room temperature, the mixture was opened air and diluted with 50% toluene/DMF to make a 1% solution (~one liter) which was filtered through a one inch pad of celite. The yellow filtrate was reduced in volume to ~300 mL, after which it was slowly added to a vigorously stirring solution of 50% MeOH/acetone (~1800 mL). A precipitated formed, which was isolated by filtration and dried under vacuum to give 4.892 g (97%) of an off-white solid. This was dissolved in CHCl₃ to make a ~8% solution which was added dropwise to vigorously stirring 6× volume of hexanes to produce a solid. After filtering and drying, the resulting solid was dissolved in CHCl₃ (1% solution) and again precipitated in 6× volume of boiling acetonitrile. The precipitated was filtered and vacuum dried to yield 2.274 g of pale yellow powdery material. GPC (THF, room temperature): Mn=10,100; Mw=20,800; Mw/Mn=2.06.

Example 3

Synthesis of Polymer 3

Synthetic pathway to polymer 3 is shown below.

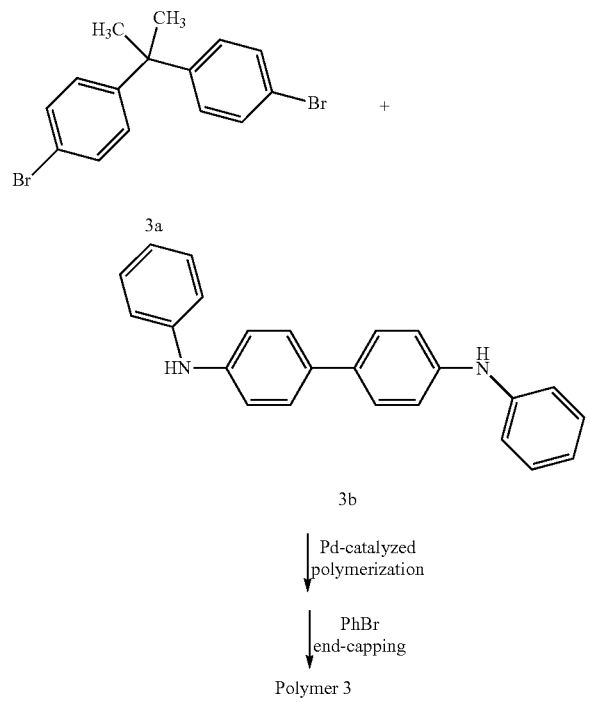

All manipulations were performed under an atmosphere of nitrogen. A 200 mL flask was charged with 4,4'-bromophenylisopropylidene (1.00 g, 2.82 mmol), N,N-diphenylbezidine (0.96 g, 2.82 mmol), NaO'Bu (0.85, 8.5 mmol), toluene (anhydrous, 30 mL), and a solution (5 mL, toluene) of tris (dibenzylideneacetone)dipalladium (0.13 g, 0.14 mmol) and P'Bu₃ (0.17 g, 0.85 mmol). The resulting reaction mixture was heated to 100° C. for 48 hrs. Bromobenzene (0.98 g, 0.62 mmol) and tris(dibenzylideneacetone)dipalladium (0.032 g) and P'Bu₃ (0.042 g). After additional 24 hrs, the reaction mixture was diluted with 50% toluene/DMF to make a 1% solution. After filtration the solvent was evaporated and the resulting solid was dissolved with CHCl₃ (1 L) then concentrated to a viscous solution, which was precipitated in hexanes and filtered twice to remove all particles. The powder was dried overnight and then dissolved in chloroform and re-precipitated in boiling CH₃CN and filtered twice. After drying a pale-yellow powder was isolated in 42% yield (0.629 g). Mn=3370; Mw=10,200; Mw/Mn=3.02.

Example 4

Synthesis of Dimer 4

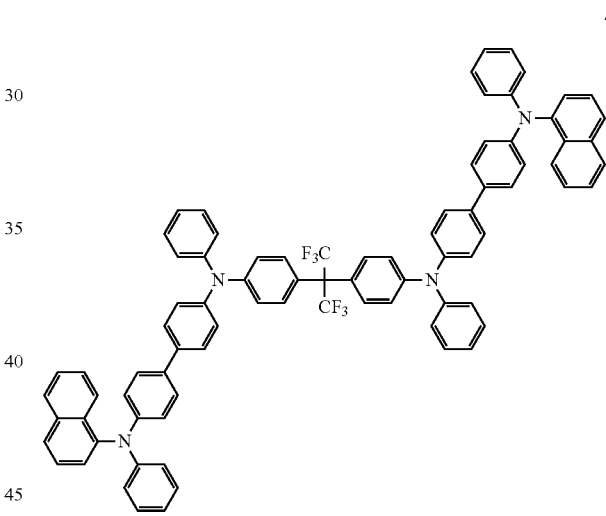

All manipulations were carried under an atmosphere of nitrogen. A Schlenk flask was charged with N,N'-diphenyl-N-naphth-1-yl-benzidine (2.00 g, 4.32 mmol), 4,4'-bromophenyl(hexaflouroisopropylidene) (0.95 g, 2.06 mmol), NaO'Bu (0.623 g, 23.8 mmol), toluene (anhydrous, 40 mL), and a solution (5 mL, toluene) of tris(dibenzylideneacetone) dipalladium (0.198 g, 0.2 mmol) and P'Bu₃ (0.262 g, 1.3 mmol). The mixture was heated to 100 C. for 12 hrs. After cooling to room temperature the solution was diluted with CH₂Cl₂ and filtered through celite. Evaporation of volatiles gave a brown solid that was dissolved in a minimum of CH₂Cl₂ and precipitate from MeOH. After filtration and drying the solid was purified by chromatography (silica, 1:2 CH₂Cl₂/Hexanes. Further purification by crystallization (CH₂Cl₂/MeOH) yielded compound 4 as an off-white powder in 81% yield (2.04 g). ¹H NMR (CD₂Cl₂, 500 MHz): δ 7.97 (d, 2H); 7.92 (d, 2H); 7.82 (d, 2H); 7.49 (m, 8H); 7.40 (m, 8H); 7.30 (t, 4H); 7.24 (m, 8H); 7.15 (m, 8H); 7.06 (m, 8H); 6.97 (t, 2H); ¹⁹F NMR (CD₂Cl₂, 376.86 MHz): δ-64.66 (s).

Example 4

Synthesis of Dimer 5

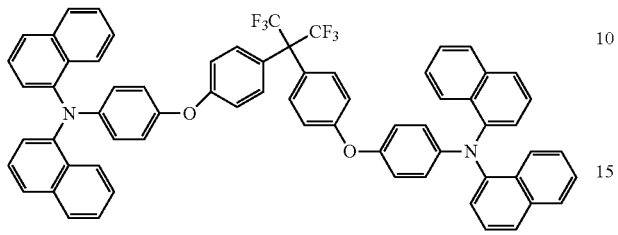

All manipulations were carried under an atmosphere of nitrogen. A round bottom flask 4",4"-(hexaflouroisopropylidene)bix(4-phenoxyaniline) (10.08 g, 19.5 mmol), 1-iodonaphthalene (14.83 g, 58.4 mmol), NaO$^t$Bu (5.61 g, 58.4 mmol), toluene (anhydrous, 300 mL), and a solution (10 mL, toluene) of tris(dibenzylideneacetone)dipalladium (1.78 g, 1.95 mmol) and P$^t$Bu$_3$ (0.98 g, 4.87 mmol). The mixture was stirred at room temperature for four days. The resulting mixture was washed with water, and the organic layer was dried over MgSO$_4$. Removal of volatiles yielded a brown oil which was purified by column chromatography using hexane (1.5 L) followed by hexane:EtOAc mixture of increasing polarity up to pure EtOAc. The desired compound 5 was isolated as a white powder (1.0 g). $^1$H NMR (CD$_2$Cl$_2$, 500 MHz): δ 8.03 (d, 1H); 7.85 (d, 1H); 7.67 (d, 1H); 7.43 (t, 1H); 7.30 (m, 3H); 7.17 (d, 1H); 6.88 (d, 1H); 6.83 (d, 1H); 6.72 (d, 1H); $^{19}$F NMR (CD$_2$Cl$_2$, 376.86 MHz): δ-64.81 (s).

What is claimed is:

1. A compound having the formula:

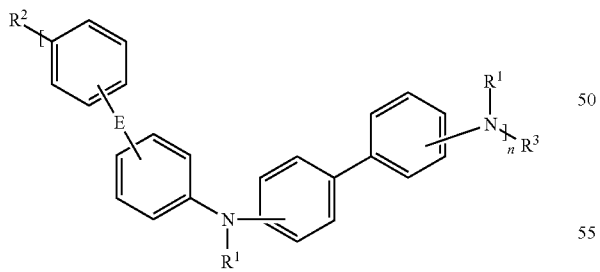

(I)

wherein:
n is an integer of at least 1;
R$^1$ is selected from aryl, heteroaryl, fluoroaryl, and fluoroheteroaryl substituted with 1 or more fluorine atoms;
R$^3$ is selected from H and R$^1$;
R$^2$ is selected from H, R$^1$, alkyl, fluoroalkyl, Cl, Br, I and an arylamino group of formula (II),

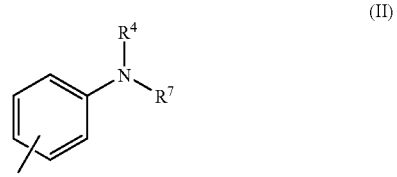

(II)

wherein R$^4$ is selected from aryl, H, R$^1$, alkyl, and fluoroalkyl;
R$^7$ is selected from aryl, heteroaryl, fluoroaryl, and fluoroheteroaryl substituted with 1 or more fluorine atoms up to 7 fluorine atoms; and
E is selected from O, S, (SiR$^5$R$^6$)$_m$ wherein m is an integer of 1 to 20, (CR$^5$R$^6$)$_m$ wherein m is an integer of 1 to 20, and combinations thereof, wherein R$^5$ and R$^6$ are each independently selected from H, F, alkyl, aryl, alkoxy, aryloxy, fluoroalkyl, fluoroaryl, fluoroalkoxy, and fluoroaryloxy and wherein R$^5$ and R$^6$ can, when taken together, form a ring, provided that when E is (CR$^5$R$^6$)$_m$, and m is 1, at least one of R$^5$ and R$^6$ is not hydrogen or a hydrocarbon, and provided that when E is (SiR$^5$R$^6$)$_m$ and m is 1, R$^3$ is selected from 1-naphthyl and 2-naphthyl.

2. The compound of claim 1, and wherein R$^5$ and R$^6$, when taken together, form a non-aromatic ring.

3. The compound of claim 2 wherein R$^1$ is different at each occurrence.

4. The compound of claim 1 wherein n is greater than 1.

5. The compound of claim 1 wherein R$^2$ is H.

6. The composition of claim 5 wherein R$^3$ is aryl.

7. The compound of claim 1 wherein R$^1$ is selected from phenyl, 1-naphthyl, and 2-naphthyl.

8. The compound of claim 1 wherein n=1, R$^2$ is H, and R$^3$ is selected from phenyl, 1-naphthyl, and 2-naphthyl.

9. A compound of formula (III):

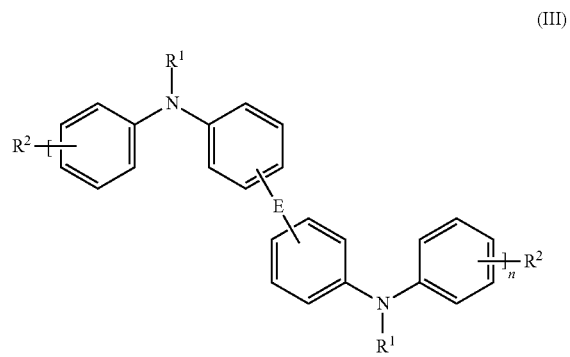

(III)

wherein
n is an integer of at least 1, R$^1$ is selected from aryl, heteroaryl, fluoroaryl, and fluoroheteroaryl; R$^2$ is selected from H, R$^1$, alkyl, fluoroalkyl, Cl, Br, I and arylamino of formula (II)

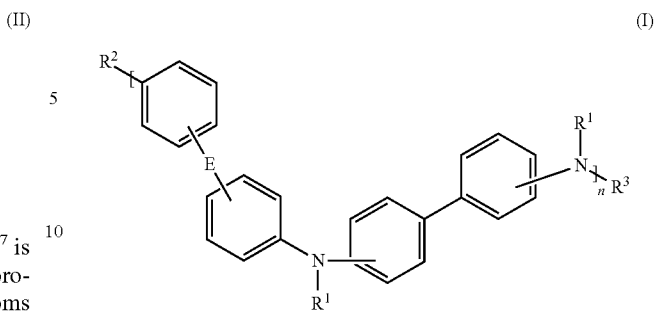

(I)

wherein:
n is an integer of at least 1;
R¹ is selected from aryl, heteroaryl, fluoroaryl, and fluoroheteroaryl substituted with 1 or more fluorine atoms;
R³ is selected from H and R¹;
R² is selected from H, R¹, alkyl, fluoroalkyl, Cl, Br, I and an arylamino group of formula (II),

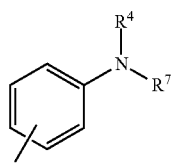

(II)

wherein R⁴ is selected from aryl, H, R¹, alkyl, and fluoroalkyl;
R⁷ is selected from aryl, heteroaryl, fluoroaryl, and fluoroheteroaryl substituted with 1 or more fluorine atoms up to 7 fluorine atoms; and
E is selected from O, S, $(SiR^5R^6)_m$ wherein m is an integer of 1 to 20, $(CR^5R^6)_m$ wherein m is an integer of 1 to 20, and combinations thereof, wherein R⁵ and R⁶ are each independently selected from H, F, alkyl, aryl, alkoxy, aryloxy, fluoroalkyl, fluoroaryl, fluoroalkoxy, and fluoroaryloxy and wherein R⁵ and R⁶ can, when taken together, form a ring, provided that when E is $(CR^5R^6)_m$, and m is 1, at least one of R⁵ and R⁶ is not hydrogen or a hydrocarbon, and provided that when E is $(SiR^5R^6)_m$ and m is 1, R³ is selected from 1-naphthyl and 2-naphthyl, and

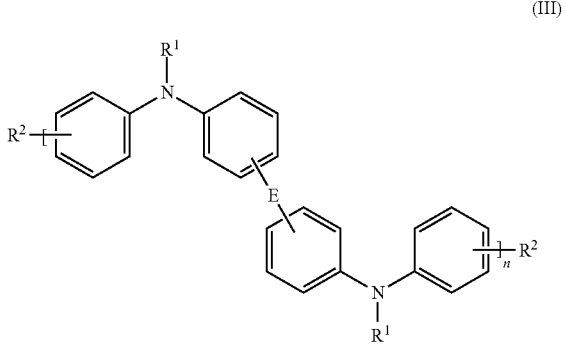

(III)

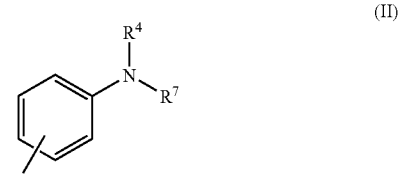

(II)

R⁴ is selected from aryl, H, R¹, alkyl, fluoroalkyl; R⁷ is selected from aryl, heteroaryl, fluoroaryl, and fluoroheteroaryl substituted with 1 or more fluorine atoms up to 7 fluorine atoms; and E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein R⁵ and R⁶ are each independently selected from H, F, alkyl, aryl, alkoxy, aryloxy, fluoroalkyl, fluoroaryl, fluoroalkoxy, and fluoroaryloxy and wherein R⁵ and R⁶ can, when taken together, form a ring, provided that when E is $(CR^5R^6)_m$, and m is 1, then n is greater than 1 and at least one of R⁵ and R⁶ is not hydrogen or a hydrocarbon, and when E=O or S, R² is not H;

wherein substituents on any one or more aromatic rings in the compound of formula (III) are selected from the group consisting of H, F, alkyl, aryl, alkoxy, aryloxy, fluoroalkyl, fluoroaryl, fluoroalkoxy, and fluoroaryloxy; and R¹ is different at each occurrence.

10. The compound of claim 9, wherein R⁵ and R⁶, when taken together, form a non-aromatic ring.

11. The compound of claim 9 wherein R² is aryl.

12. The compound of claim 9 wherein R⁴ is aryl.

13. The compound of claim 9 wherein R¹ is selected from phenyl, 1-naphthyl, and 2-naphthyl.

14. The compound of claim 9 wherein n=1, R² is H, and R¹ is selected from phenyl, 1-naphthyl, and 2-naphthyl.

15. The compound of claim 9 wherein at least one aromatic ring in the compound of formula (III) has a substituent.

16. The compound of claim 9 wherein substituents on two neighboring aromatic rings in the compound of formula (III) together form an aromatic or non-aromatic ring.

17. The compound of claim 9 wherein adjacent substituents on at least one aromatic ring together form a fused aromatic or non-aromatic ring.

18. An electronic device comprising at least one layer comprising at least one compound selected from the compounds of claim 1 or claim 9.

19. The device of claim 18, wherein the layer is a charge transport layer.

20. The device of claim 18, wherein the layer is a light-emitting layer.

21. The device of claim 18, wherein the device is selected from a light-emitting diode, a light-emitting diode display, a laser diode, a photodetector, photoconductive cell, photoresistor, photoswitch, phototransistor, phototube, IR-detector, photovoltaic device, solar cell, transistor or diode.

22. A composition comprising a compound of at least one compound selected from:

wherein n is an integer of at least 1, $R^1$ is selected from aryl, heteroaryl, fluoroaryl, and fluoroheteroaryl; $R^2$ is selected from H, $R^1$, alkyl, fluoroalkyl, Cl, Br, I and arylamino of formula (II)

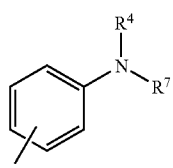
(II)

$R^4$ is selected from aryl, H, $R^1$, alkyl, fluoroalkyl; $R^7$ is selected from aryl, heteroaryl, fluoroaryl, and fluoroheteroaryl substituted with 1 or more fluorine atoms up to 7 fluorine atoms; and E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon, and when E=O or S, $R^2$ is not H;

wherein substituents on any one or more aromatic rings in the compound of formula (III) are selected from the group consisting of H, F, alkyl, aryl, alkoxy, aryloxy, fluoroalkyl, fluoroaryl, fluoroalkoxy, and fluoroaryloxy: and $R^1$ is different at each occurrence.

23. A process for producing a polymer, comprising:

(a) providing two or more compounds having the formulae (I) or (III):

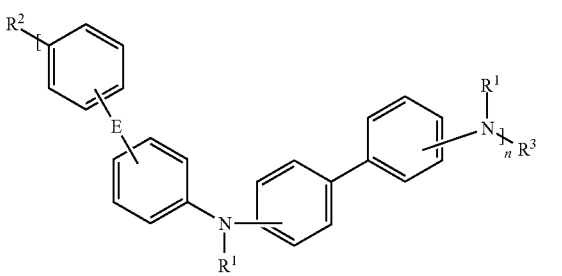
(I)

wherein:

n is an integer of at least 1;

$R^1$ is selected from aryl, heteroaryl, fluoroaryl, and fluoroheteroaryl substituted with 1 or more fluorine atoms;

$R^3$ is selected from H and $R^1$;

$R^2$ is selected from H, $R^1$, alkyl, fluoroalkyl, Cl, Br, I and an arylamino group of formula (II),

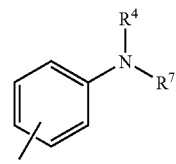
(II)

wherein $R^4$ is selected from aryl, H, $R^1$, alkyl, and fluoroalkyl; $R^7$ is selected from aryl, heteroaryl, fluoroaryl, and fluoroheteroaryl substituted with 1 or more fluorine atoms up to 7 fluorine atoms; and E is selected from O, S, $(SiR^5R^6)_m$ wherein m is an integer of 1 to 20, $(CR^5R^6)_m$ wherein m is an integer of 1 to 20, and combinations thereof, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon or

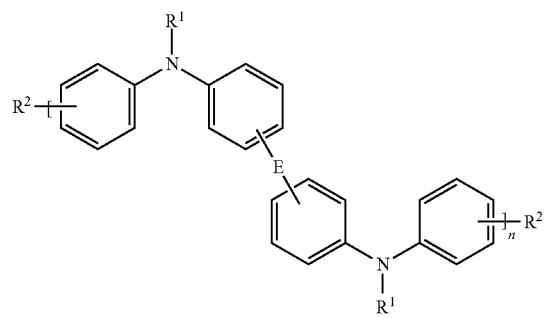
(III)

wherein n is an integer of at least 1, $R^1$ is selected from aryl, heteroaryl, fluoroaryl, and fluoroheteroaryl and may be different at each occurrence; $R^2$ is selected from H, $R^1$, alkyl, fluoroalkyl, Cl, Br, I and arylamino of formula (II)

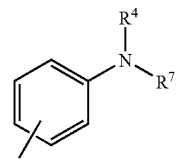
(II)

$R^4$ is selected from aryl, H, $R^1$, alkyl, fluoroalkyl; $R^7$ is selected from aryl, heteroaryl, fluoroaryl, and fluoroheteroaryl substituted with 1 or more fluorine atoms, preferably up to 7 fluorine atoms; and E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon, and when E=O, $R^2$ is not H;

(b) reacting said compounds in the presence of a copper, nickel, or palladium catalyst while maintaining said compounds at a temperature of 22° C. to 150° C. for 24 to 92 hours, to form a first polymer;

(c) treating said polymer with an endcapping group to form a capped polymer; and (d) further reacting said capped polymer for 24 to 48 hours to produce said polymer.

* * * * *